United States Patent [19]

Fest et al.

[11] Patent Number: 4,886,832
[45] Date of Patent: Dec. 12, 1989

[54] FUNGICIDAL BENZALDOXIME DERIVATIVES

[75] Inventors: Christa Fest, Wuppertal; Kurt Findeisen, Odenthal; Wilhelm Brandes, Leichlingen; Stefan Dutzmann, Duesseldorf; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 166,335

[22] Filed: Mar. 10, 1988

[30] Foreign Application Priority Data

Mar. 14, 1987 [DE] Fed. Rep. of Germany ....... 3708320

[51] Int. Cl.$^4$ ............................................. A01N 47/12
[52] U.S. Cl. .................................... 514/477; 514/640; 514/448; 564/254; 564/255; 549/71
[58] Field of Search ................ 564/254, 255; 514/640, 514/448, 477; 549/71

[56] References Cited

U.S. PATENT DOCUMENTS

| | | | |
|---|---|---|---|
| 3,903,303 | 9/1975 | Gutman | 514/640 |
| 4,052,194 | 10/1977 | Wilcox | 504/254 |
| 4,449,999 | 5/1984 | Sturp et al. | 71/103 |
| 4,497,745 | 2/1985 | Martin | 71/103 |
| 4,566,901 | 1/1986 | Martin et al. | 71/103 |
| 4,716,176 | 9/1987 | Fest et al. | 564/255 |
| 4,747,678 | 5/1988 | Benko et al. | 514/640 |

OTHER PUBLICATIONS

Fest et al, Chem. Abst., vol. 106, #175,961y (1987).
Lee et al, "Synthesis of Ketoximino Esters as Antihistaminics", J. Pharm. Sci., 56 (1967), No. 10, pp. 1354–1357.

*Primary Examiner*—James H. Reamer
*Attorney, Agent, or Firm*—Sprung Horn Kramer & Woods

[57] ABSTRACT

Fungicidally active benzaldoxime derivatives of the formula

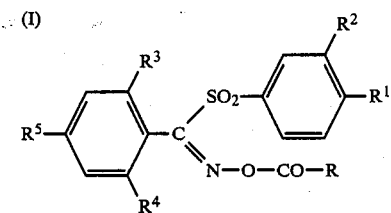

(I)

in which
R represents alkyl, alkoxy, halgenoalkyl, halogenoalkoxy or alkenyloxy, or aryl or aryloxy, in each case optionally mono- or polysubstituted by identical or different substituents, aralkyloxy which is optionally mono- or polysubstituted in the aryl radical by identical or different substituents, or represents cycloalkoxy which is optionally mono- or polysubstituted by identical or different substituents, or represents a heterocyclic radical which is optionally mono- or polysubstituted by identical or different substituents,
$R^1$ represents hydrogen, halogen, alkyl or alkoxy,
$R^2$ represents hydrogen, alkyl or halogenoalkyl,
$R^3$ represents hydrogen or halogen,
$R^4$ represents halogen and
$R^5$ represents hydrogen or halogen.

12 Claims, No Drawings

FUNGICIDAL BENZALDOXIME DERIVATIVES

The present invention relates to new benzaldoxime derivatives, a process for their preparation and their use as agents for combating pests, in particular as fungicides.

A number of aldoxime derivatives are already known. Thus, for example, arylsulphonylbenzaldoximes, such as α-phenylsulphonyl-2,6-dichloro-benzaldoxime, and their use as agents for combating pests, above all their use in agents for combating bunt of wheat, are known (compare Swiss Patent No. 423,350). Phenyl-pyridinealdoximes, such as, for example, phenyl-O-ethylcarbonylpyridinealdoxime, and their antihistamine action are furthermore known (compare J. Pharm. Sci. 56(1967) No. 10, pages 1354–1357).

New benzaldoxime derivatives of the general formula (I)

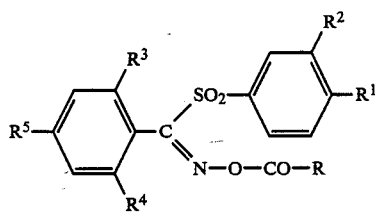

in which
R represents alkyl, alkoxy, halogenoalkyl, halogenoalkoxy or alkenyloxy, or aryl or aryloxy, in each case optionally mono- or polysubstituted by identical or different substituents, aralkyloxy which is optionally mono or polysubstituted in the aryl radical by identical or different substituents, or represents cycloalkoxy which is optionally mono- or polysubstituted by identical or different substituents, or represents a heterocyclic radical which is optionally mono- or polysubstituted by identical or different substituents,
$R^1$ represents hydrogen, halogen, alkyl or alkoxy,
$R^2$ represents hydrogen, alkyl or halogenoalkyl,
$R^3$ represents hydrogen or halogen,
$R^4$ represents halogen and
$R^5$ represents hydrogen or halogen,
have been found.

It has furthermore been found that the benzaldoxime derivatives of the formula (I)

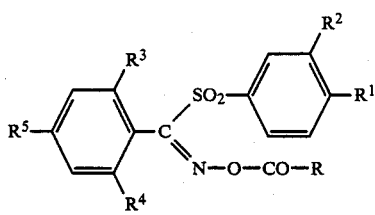

in which
R represents alkyl, alkoxy, halogenoalkyl, halogenoalkyl or alkenyloxy, or aryl or aryloxy, in each case optionally mono- or polysubstituted by identical or different substituents, aralkyloxy which is optionally mono- or polysubstituted in the aryl radical by identical or different substituents, or represents cycloalkoxy which is optionally mono- or polysubstituted by identical or different substitu-
ents, or represents a heterocyclic radical which is optionally mono- or polysubstituted by identical or different substituents,
$R^1$ represents hydrogen, halogen, alkyl or alkoxy,
$R^2$ represents hydrogen, alkyl or halogenoalkyl,
$R^3$ represents hydrogen or halogen,
$R^4$ represents halogen and
$R^5$ represents hydrogen or halogen,
are obtained by a process in which phenylsulphonylbenzaldoximes of the general formula (II)

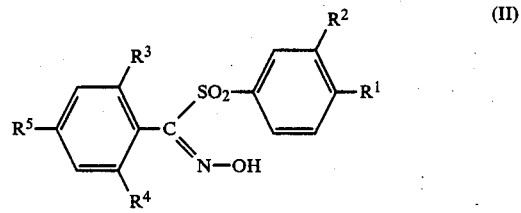

in which
$R^1$, $R^2$, $R^3$, $R^4$ and $R^5$ have the abovementioned meanings,
are reacted with carbonyl compounds of the general formula (III)

$$X-CO-R \qquad (III)$$

in which
R has the abovementioned meanings and
X represents a halogen atom, preferably chlorine, or represents the radical —O—COR,
wherein
R has the abovementioned meaning,
if appropriate in the presence of a solvent or diluent and if appropriate in the presence of acid-binding agent.

The benzaldoxime derivatives of the formula (I) according to the invention have powerful biological properties, above all fungicidal properties.

Surprisingly, the compounds according to the invention thereby exhibits a considerably higher activity, above all a fungicidal activity, than the compounds known from the prior art which are very closely related compounds structurally and/or from the point of view of their action.

The compounds of the formula (I) according to the invention can be obtained as syn- or anti-isomers or as mixtures thereof in varying compositions. The invention thus relates both to the pure isomers and to the isomer mixtures.

The alkyl radicals R, $R^1$ and $R^2$ and the alkyl parts in the alkoxy radicals in R and $R^1$ can be straight-chain or branched and preferably contain in each case 1 to 6, in particular 1 to 4, carbon atoms. Examples which may be mentioned are: methyl, ethyl, n-propyl, iso-propyl, n-butyl, sec.-butyl, iso-butyl, tert.-butyl, n-pentyl, iso-pentyl, sec.-pentyl, n-hexyl, sec.-hexyl, methoxy, ethoxy, n-propoxy, iso-propoxy, n-butoxy, iso-butoxy, sec.-butoxy, tert.-butoxy, n-pentoxy, iso-pentoxy, sec.-pentoxy, n-hexoxy and sec.-hexoxy.

The alkenyloxy radical in R preferably contains 2 to 6, in particular 2 to 5 and particularly preferably 2 or 3, carbon atoms. Examples which may be mentioned are: vinyl, allyl, propen-1-yl, butenyl and pentenyl.

The halogenoalkyl parts in R and $R^2$ in the radicals halogenoalkyl and halogenoalkoxy preferably contain in each case 1 to 6, in particular 1 to 4 and particularly preferably 1 to 2, carbon atoms and preferably 1 to 9, in particular 1 to 5 and particularly preferably 1 to 4, identical or different halogen atoms. Examples which may be mentioned are: monochloromethyl, trichloromethyl, trifluoromethyl, dichlorofluoromethyl, trichloroethyl, tetrachloroethyl, trichloromethoxy, trichloroethoxy and tetrachloroethoxy.

Halogen in R to $R^5$, including in the radicals such as halogenoalkyl and halogenoalkoxy or in the aryl substituents and the like, denotes fluorine, chlorine, bromine or iodine, in particular fluorine or chlorine, unless defined specifically elsewhere.

Aryl, including in the aryloxy radical in R, can represent an aromatic hydrocarbon radical with 6 to 10 carbon atoms. Examples which may be mentioned are phenyl and naphthyl. Phenyl is preferred.

Aralkyl in the aralkoxy in R can represent a radical with 7 to 18 carbon atoms, it being possible for a straight-chain or branched alkyl radical ($C_1$ to $C_6$) to be substituted by an aromatic radical ($C_6$ to $C_{10}$). Examples which may be mentioned are benzyl, phenyl-ethyl and phenyl-propyl. Benzyl is preferred.

Cycloalkyl in cycloalkoxy can represent a cyclic, preferably a monocyclic, hydrocarbon radical with 5 to 7 carbon atoms. Examples which may be mentioned are cyclopentyl, cyclohexyl and cycloheptyl. Cyclopentyl and cyclohexyl are preferred.

A heterocyclic radical can be a saturated or partly or completely unsaturated 5- to 8-membered ring, preferably a 5- or 6-membered ring, with 1 to 3, preferably 1 to 2, hetero atoms and in particular 1 hetero atom, hetero atoms which may be mentioned being sulphur, oxygen or nitrogen, in particular sulphur.

The aryl, aryloxy and aralkyloxy mentioned can be unsubstituted or substituted; possible substituents are 1 to 5, preferably 1 to 3, substituents and particularly preferably 1 or 2 substituents from the group comprising lower alkyl groups with 1 to 4 carbon atoms (methyl, ethyl, propyl, isopropyl, butyl and isobutyl), lower alkoxy groups with 1 to 4 carbon atoms (methoxy, ethoxy, propoxy, isopropoxy, butoxy and isobutoxy) and the halogens (fluorine, chlorine and bromine). Other substituents can be: the nitro group and the acetyl group.

The cycloalkoxy mentioned can be unsubstituted or substituted; possible substituents are 1 to 5, preferably 1 to 3 and particularly preferably 1 to 3, substituents from the group comprising lower alkyl groups with 1 to 4 carbon atoms (methyl, ethyl, propyl, i-propyl, n- and s-butyl, i-butyl and t-butyl).

The heterocyclic radical mentioned can be unsubstituted or substituted. Possible substituents are 1 to 3, preferably 1, substituents from the group comprising lower alkyl groups with 1 to 4 carbon atoms, as listed above.

Formula (I) provides a general definition of the benzaldoxime derivatives according to the invention. Preferred compounds of the formula (I) are those in which R represents straight-chain or branched alkyl with 1 to 6 carbon atoms, or represents straight-chain or branched alkoxy with 1 to 6 carbon atoms, or represents halogenoalkyl or halogenoalkoxy with in each case 1 to 6 carbon atoms in the straight-chain or branched halogenoalkyl radical and 1 to 9 identical or different halogen atoms, or represents straight-chain or branched alkenyloxy with 2 or 6 carbon atoms, or represents aryl or aryloxy which have 6 to 10 carbon atoms and are unsubstituted or in each case substituted by one to five identical or different substituents from the group comprising straight-chain or branched alkyl with 1 to 4 carbon atoms, straight-chain or branched alkoxy with 1 to 4 carbon atoms, halogen, nitro and acetyl, or represents aralkyloxy which has 6 to 12 carbon atoms in the aryl radical and 1 to 6 carbon atoms in the straight-chain or branched alkyl radical and is unsubstituted or substituted by one to five identical or different substituents from the group comprising straight-chain or branched alkyl and alkoxy with 1 to 4 carbon atoms, halogen, nitro and acetyl, or represents cycloalkoxy which has 5 to 7 carbon atoms in the cycloalkyl part and is unsubstituted or substituted by one to five identical or different substituents from the group comprising straight-chain or branched alkyl with 1 to 4 carbon atoms, or represents a saturated or partly or completely unsaturated heterocyclic radical which has 5 to 8 ring members, can contain 1 to 3 hetero atoms and is unsubstituted or substituted by one to three identical or different substituents from the group comprising straight-chain or branched alkyl with 1 to 4 carbon atoms;

$R^1$ represents hydrogen, halogen, straight-chain or branched alkyl with 1 to 6 carbon atoms or straight-chain or branched alkoxy with 1 to 6 carbon atoms, $R^2$ represents hydrogen or straight-chain or branched alkyl with 1 to 6 carbon atoms, or represents straight-chain or branched halogenoalkyl with 1 to 6 carbon atoms and 1 to 9 identical or different halogen atoms, $R^3$ represents hydrogen or halogen, $R^4$ represents halogen and $R^5$ represents hydrogen or halogen.

Particularly preferred compounds of the formula (I) are those in which

R represents straight-chain or branched alkyl with 1 to 4 carbon atoms, or represents straight-chain or branched alkoxy with 1 to 4 carbon atoms, or represents halogenoalkyl or halogenoalkoxy with in each case 1 to 4 carbon atoms in the straight-chain or branched halogenoalkyl radical and 1 to 5 identical or different halogen atoms, or represents straight-chain or branched alkenyloxy with 2 to 5 carbon atoms, or represents phenyl or phenoxy which are unsubstituted or in each case substituted by one to five identical or different substituents from the group comprising straight-chain or branched alkyl with 1 to 3 carbon atoms, straight-chain or branched alkoxy with 1 to 3 carbon atoms, halogen, nitro and acetyl, or represents benzyloxy, phenethyloxy or phenylpropyloxy which are unsubstituted or substituted by one to three identical or different substituents from the group comprising straight-chain or branched alkyl and alkoxy with 1 to 3 carbon atoms, halogen, nitro and acetyl, or represents cycloalkoxy which has 5 to 7 carbon atoms in the cycloalkyl part and is unsubstituted or substituted by one to three identical or different substituents from the group comprising straight-chain or branched alkyl with 1 to 3 carbon atoms, or represents a saturated, partly saturated or unsaturated heterocyclic radical which has 5 to 7 ring members, can contain 1 or 2 sulphur, nitrogen and- /or oxygen atoms and is unsubstituted or monosubstituted by straight-chain or branched alkyl with 1 to 3 carbon atoms;

$R^1$ represents hydrogen, halogen, straight-chain or branched alkyl with 1 to 4 carbon atoms or straight-chain or branched alkoxy with 1 to 4 carbon atoms, $R^2$ represents hydrogen or straight-chain or branched alkyl with 1 to 4 carbon atoms, or represents straight-chain or branched halogenoalkyl with 1 to 4 carbon atoms and 1 to 5 identical or different halogen atoms, $R^3$ represents hydrogen or halogen, $R^4$ represents halogen and $R^5$ represents hydrogen or halogen.

Especially preferred compounds of the formula (I) are those in which

R represents straight-chain or branched alkyl with 1 to 6 carbon atoms, or represents straight-chain or branched alkoxy with 1 to 6 carbon atoms, or represents halogenoalkyl or halogenoalkoxy with in each case 1 or 2 carbon atoms in the straight-chain or branched halogenoalkyl radical and 1 to 4 identical or different halogen atoms, or represents straight-chain or branched alkenyloxy with 2 or 3 carbon atoms, or represents phenyl or phenoxy which are unsubstituted or in each case substituted by one or two identical or different substituents from the group comprising alkyl with 1 or 2 carbon atoms, alkoxy with 1 or 2 carbon atoms, halogen, nitro and acetyl, or represents benzyl which is unsubstituted or substituted by one to three identical or different substituents from the group comprising alkyl and alkoxy with 1 or 2 carbon atoms and halogen, or represents cycloalkoxy which has 5 or 6 carbon atoms in the cycloalkyl part and is unsubstituted or substituted by one to three identical or different substituents from the group comprising alkyl with 1 or 2 carbon atoms, or represents an unsaturated heterocyclic radical which has 5 or 6 ring members, can contain nitrogen atoms or a sulphur atom and is unsubstituted or substituted by one or two identical or different substituents from the group comprising alkyl with 1 or 2 carbon atoms:

$R^1$ represents hydrogen, halogen, alkyl with 1 or 2 carbon atoms or alkoxy with 1 or 2 carbon atoms, $R^2$ represents hydrogen or alkyl with 1 or 2 carbon atoms, or represents halogenoalkyl with 1 or 2 carbon atoms and 1 to 3 identical or different halogen atoms, $R^3$ represents hydrogen or halogen, $R^4$ represents halogen and $R^5$ represents hydrogen or halogen.

Compounds of the formula (I) which may be mentioned in particular are those in which R represents methyl, ethyl, methoxy, ethoxy, n-propoxy, iso-propoxy, iso-butoxy, allyloxy, 2,2,2-trichloroethoxy, benzyloxy, chloromethyl, phenyl, 2,6-dichlorophenyl, 2,4-dichlorophenyl, phenoxy, thienyl or cyclohexyloxy, $R^1$ represents hydrogen, fluorine, chlorine, methyl or methoxy, $R^2$ represents hydrogen or trifluoromethyl, $R^3$ represents hydrogen, fluorine or chlorine, $R^4$ represents fluorine or chlorine and $R^5$ represents hydrogen or chlorine.

If 2,6-difluoro-α-(4-methylphenylsulphonyl)-benzaldoxime and acetic anhydride are used as starting compounds, the course of the reaction in the process according to the invention can be represented by the following equation:

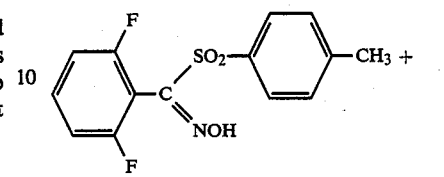

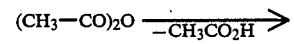

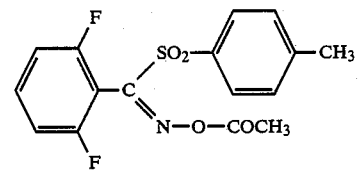

The phenylsulphonyl-benzaldoximes of the general formula (II) required as starting substances for carrying out the process according to the invention are known in some cases. The known compounds and the new compounds can be prepared by analogous processes, for example by the process described in Swiss Patent No. 423,350 in Example VII, by a procedure in which α-halogeno-benzaldoximes of the formula (IV)

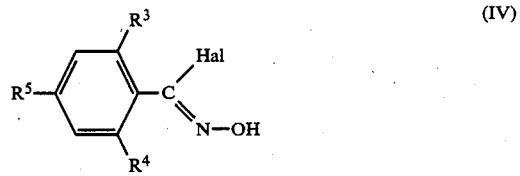

wherein $R^3$, $R^4$ and $R^5$ have the abovementioned meaning and Hal represents halogen, preferably chlorine, are reacted with benzenesulphinic acids of the formula (V)

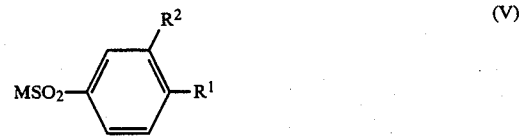

in which $R^1$ and $R^2$ have the abovementioned meanings and M represents hydrogen or one equivalent of an alkali metal, if appropriate in the presence of a solvent and if appropriate in the presence of an acid acceptor.

The sulphinic acids are known compounds.

Formula (III) provides a definition of the carbonyl compounds furthermore required as starting substances. These are known compounds of organic chemistry.

If appropriate, the process according to the invention can be carried out in the presence of a solvent or diluent. Possible solvents or diluents are in principle all the inert organic solvents. Solvents which are preferably used are hydrocarbons, which may be chlorinated, such as, for example, benzene, toluene, xylene, methylene chloride, chloroform, carbon tetrachloride, chlorobenzene and dichlorobenzene, and furthermore ethers, such as diethyl and dibutyl ether, glycol dimethyl ether and diglycol dimethyl ether, tetrahydrofuran and dioxane, and moreover ketones, such as acetone, methyl ethyl ketone, methyl isopropyl ketone and methyl isobutyl ketone, and also esters, such as methyl and ethyl acetate, and furthermore nitriles, such as, for example, acetonitrile, propionitrile, benzonitrile and glutaric acid dinitrile, and moreover amides, such as, for example, dimethylformamide.

Possible acid-binding agents for the process according to the invention are the customary inorganic or organic acid binders. Acid binders which may be mentioned are: for example, tertiary amines, such as triethylamine, pyridine, triethylenediamine and others.

The reaction temperature of the process according to the invention can be varied within a substantial temperature range. The reaction is in general carried out between 0° C. and 120° C., preferably between 20° C. and 70° C.

The reaction is usually carried out under normal pressure. In carrying out the process according to the invention, the compounds of the formula (II) are in general taken in a solvent with equimolar amounts of the acid binder, and the carbonyl compound of the formula (III) is added, preferably likewise in equimolar amounts. Working up is carried out by generally customary methods.

A particular embodiment should also be mentioned. If X denotes —O—COR, that is to say, thus, the carboxylic acid anhydride of the formula (III) are used, the reaction is carried out without a solvent but with a large excess of the anhydride, which then simultaneously serves as the starting substance and solvent. Working up is likewise carried out by customary processes.

The active compounds according to the invention have a powerful biological action and can be used in practice for combating undesirable pests. The active compounds are suitable for use as agents for combating pests, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris pv. oryzae*; Pseudomonas species, such as, for example, *Pseudomonas syringae pv. lachyrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example *Peronospora; pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nudea*or Ustilago avenae; Pellicularia species, such as, for example, *Pellicularia sasakii*; Pyricularia species, such as, for example, *Pyricularia oryzae*; Fusarium species, such as, for example, *Fusarium culmorum*; Botrytis, such as, for example *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seeds, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.001 to 10 g, are generally required.

For the treatment of soil, active compound concentrations of 0.00001 to 0.1% by weight, preferably 0.0001 to 0.02%, are required at the place of action.

The compounds of the formula (I) according to the invention exhibit a particularly good action against causative organisms of vegetable and fruit diseases, cereal diseases and rice diseases, of which there may be mentioned Venturia species, *Phytophthora infestans, Leptosphaeria nodorum* and *Pyricularia oryzae,* and there may furthermore be mentioned *Pyrenophora teres, Cochliobolus sativus* and *Puccinia recondita,* and in an appropriate concentration an in vitro action against bacteria is also to be recorded.

In appropriate concentrations, the substances according to the invention also exhibit herbicidal actions.

Use Examples:

The compound shown below was employed as the comparison substance in the use examples which follow:

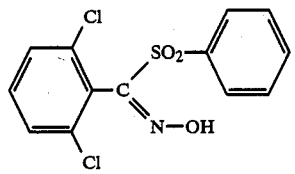

α-Benzsulphonyl-2,6-dichlorobenzaldoxime (known from Swiss Patent No. 423,350; Example VII).

Example A

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown by the compounds according to the invention at an active compound concentration of, for example, 0.025%.

Example B

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

A clearly superior activity compared with the prior art is shown by most of the compounds according to the invention at an active compound concentration of 0.025% by weight.

Example C

Phytophthora Test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

A clearly superior activity compared with the prior art is shown by many of the compounds according to the invention at 10 ppm.

Example D

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

A clearly superior activity compared with the prior art is shown by the compounds at an active compound concentration in 10 ppm.

Preparation Examples

Example 1

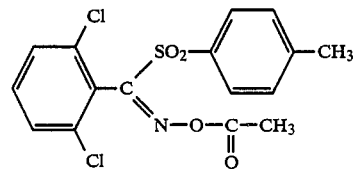

25.8 g (0.075 m) of 2,6-dichloro-α-(4-methylphenylsulphonyl)-benzaldoxime are heated at 70°–80° C. with 100 ml of acetic anhydride for 24 hours. The reaction mixture is then concentrated and the hot residue is stirred with isopropanol, filtered off hot with suction, washed and dried. 23.8 g (82% of theory) of the undesired product with a melting point of 179° C. are obtained.

Compounds of the formula (I)

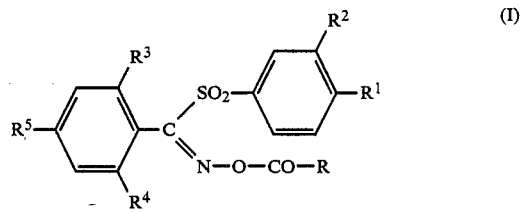

are prepared analogously:

| Example No. | R | $R^1$ | $R^2$ | $R^3$ | $R^4$ | $R^5$ | Physical data (Melting point °C.) |
|---|---|---|---|---|---|---|---|
| 2 | —OC$_3$H$_7$-i | —CH$_3$ | H | Cl | Cl | H | 201 |
| 3 | —OC$_3$H$_7$-i | H | H | Cl | Cl | H | 158 |
| 4 | —OC$_3$H$_7$-i | Cl | H | Cl | Cl | H | 174 |
| 5 | —OCH$_3$ | —CH$_3$ | H | Cl | Cl | H | 178 |
| 6 | —OC$_2$H$_5$ | —CH$_3$ | H | Cl | Cl | H | 185 |
| 7 | —OCH$_2$—CH=CH$_2$ | —CH$_3$ | H | Cl | Cl | H | 158 |
| 8 | —OCH$_3$ | Cl | H | Cl | Cl | H | 164 |
| 9 | —OC$_2$H$_5$ | Cl | H | Cl | Cl | H | 142 |
| 10 | —OCH$_2$—CH=CH$_2$ | Cl | H | Cl | Cl | H | 133 |
| 11 | —OCH$_3$ | H | H | Cl | Cl | H | 112 |
| 12 | —OC$_2$H$_5$ | H | H | Cl | Cl | H | 137 |
| 13 | —OCH$_2$—CH=CH$_2$ | H | H | Cl | Cl | H | 120 |
| 14 | —OC$_4$H$_9$-i | H | H | Cl | Cl | H | 138 |
| 15 | —OC$_4$H$_9$-i | —CH$_3$ | H | Cl | Cl | H | 183 |
| 16 | —OC$_2$H$_5$ | —CH$_3$ | H | H | Cl | H | 127 |
| 17 | —OCH$_3$ | —CH$_3$ | H | H | Cl | H | 133 |
| 18 | —OC$_3$H$_7$-i | —CH$_3$ | H | H | Cl | H | 113 |
| 19 | —OCH$_2$—CH=CH$_2$ | —CH$_3$ | H | H | Cl | H | 103 |
| 20 | —OC$_2$H$_5$ | —CH$_3$ | H | F | F | H | 196 |
| 21 | —OC$_2$H$_5$ | Cl | H | F | F | H | 131 |
| 22 | —OCH$_2$—C$_6$H$_5$ | —CH$_3$ | H | H | Cl | H | 125 |
| 23 | —OC$_4$H$_9$-i | —CH$_3$ | H | H | Cl | H | 100 |
| 24 | —OC$_2$H$_5$ | H | H | F | F | H | 168 |
| 25 | —OC$_2$H$_5$ | F | H | Cl | Cl | H | 173 |
| 26 | —OC$_2$H$_5$ | —OCH$_3$ | H | Cl | Cl | H | 157 |
| 27 | —OC$_2$H$_5$ | H | —CF$_3$ | Cl | Cl | H | 112 |
| 28 | —OCH$_3$ | F | H | Cl | Cl | H | 171 |
| 29 | —OC$_3$H$_7$-i | F | H | Cl | Cl | H | 165 |
| 30 | —OCH$_2$—CH=CH$_2$ | F | H | Cl | Cl | H | 127 |

-continued

| Example No. | R | $R^1$ | $R^2$ | $R^3$ | $R^4$ | $R^5$ | Physical data (Melting point °C.) |
|---|---|---|---|---|---|---|---|
| 31 | $-OC_2H_5$ | F | H | F | F | H | 172 |
| 32 | $-OCH_2-CCl_3$ | $-CH_3$ | H | H | Cl | H | 149 |
| 33 | $-O-\langle\text{cyclohexyl}\rangle$ H | $-CH_3$ | H | H | Cl | H | 147 |
| 34 | $-OC_2H_5$ | $-OCH_3$ | H | Cl | F | H | 143 |
| 35 | $-CH_3$ | H | H | Cl | Cl | H | 152 |
| 36 | $-CH_3$ | Cl | H | Cl | Cl | H | 170 |
| 37 | $-CH_2Cl$ | $-CH_3$ | H | Cl | Cl | H | 172 |
| 38 | $-CH_2Cl$ | H | H | Cl | Cl | H | 169 |
| 39 | $-CH_3$ | $-CH_3$ | H | H | Cl | H | 103 |
| 40 | 2,6-dichlorophenyl | $-Cl$ | H | Cl | Cl | H | 200–202 |
| 41 | 2-thienyl | Cl | H | Cl | Cl | H | 178–180 |
| 42 | 2,6-dichlorophenyl | $-CH_3$ | H | Cl | Cl | H | 203–205 |
| 43 | 2-thienyl | $-CH_3$ | H | Cl | Cl | H | 173–175 |
| 44 | $-OCH_3$ | $-CH_3$ | H | Cl | F | H | 172 |
| 45 | $-OC_2H_5$ | $-CH_3$ | H | Cl | F | H | 192 |
| 46 | $-OC_3H_7$-i | $-CH_3$ | H | Cl | F | H | 161 |
| 47 | $-OC_4H_9$-i | $-CH_3$ | H | Cl | F | H | 169 |
| 48 | $-OCH_2-CH=CH_2$ | $-CH_3$ | H | Cl | F | H | 147 |
| 49 | $-OCH_2-CCl_3$ | $-CH_3$ | H | Cl | F | H | 173 |
| 50 | $-OC_2H_5$ | Cl | H | Cl | F | H | 148 |
| 51 | $-OCH_2-CH=CH_2$ | $-CH_3$ | H | H | Cl | Cl | 75 |
| 52 | $-OC_2H_5$ | $-CH_3$ | H | H | Cl | Cl | 77 |
| 53 | $-OCH_3$ | $-CH_3$ | H | H | Cl | Cl | |
| 54 | $-OC_3H_7$-i | $-CH_3$ | H | H | Cl | Cl | |
| 55 | $-OC_4H_9$-i | Cl | H | Cl | Cl | H | 145 |
| 56 | $-CH_2Cl$ | Cl | H | Cl | Cl | H | 132 |
| 57 | $-O-C_6H_5$ | $-CH_3$ | H | Cl | Cl | H | 132 |
| 58 | $-OCH_3$ | $-CH_3$ | H | F | F | H | 175 |
| 59 | $-CH_3$ | $-CH_3$ | H | F | F | H | 148 |
| 60 | $-O-CH_2-CH=CH_2$ | $-CH_3$ | H | F | F | H | 140 |
| 61 | $-OCH_2CCl_3$ | $-CH_3$ | H | F | F | H | 128 |
| 62 | phenyl | Cl | H | Cl | Cl | H | 206 |
| 63 | phenyl | $CH_3$ | H | Cl | Cl | H | 193 |

-continued

| Example No. | R | $R^1$ | $R^2$ | $R^3$ | $R^4$ | $R^5$ | Physical data (Melting point °C.) |
|---|---|---|---|---|---|---|---|
| 64 | 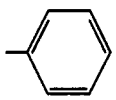 | $CH_3$ | H | H | Cl | H | 120 |
| 65 | $-CH_2Cl$ | $CH_3$ | H | H | Cl | H | 123 |
| 66 | $-OCH_3$ | H | H | H | Cl | H | 145 |
| 67 | $-OC_4H_9\text{-}i$ | H | H | H | Cl | H | 122 |
| 68 | $-OC_2H_5$ | H | H | H | Cl | H | 107 |
| 69 | $-OCH_2CCl_3$ | H | H | H | Cl | H | 120 |
| 70 | $-O-CH_2-CH=CH_2$ | H | H | H | Cl | H | 64 |
| 71 | $-OCH_3$ | Cl | H | H | Cl | H | 145–47 |
| 72 | $-OC_4H_9\text{-}i$ | Cl | H | H | Cl | H | 122 |
| 73 | $-OC_2H_5$ | Cl | H | H | Cl | H | 121 |
| 74 | $-OCH_2CCl_3$ | Cl | H | H | Cl | H | 124 |
| 75 | $-O-CH_2-CH=CH_2$ | Cl | H | H | Cl | H | 104 |
| 76 | $-OCH_3$ | Cl | H | Cl | F | H | 160 |
| 77 | $-O-CH_2-CH=CH_2$ | Cl | H | Cl | F | H | 104 |
| 78 | $-OC_4H_9\text{-}i$ | Cl | H | Cl | F | H | 109 |
| 79 | $-OCH_2CCl_3$ | Cl | H | Cl | F | H | 171 |
| 80 | $-CH_3$ | Cl | H | H | Cl | H | 131 |
| 81 | $-CH_2Cl$ | Cl | H | H | Cl | H | 108 |
| 82 | 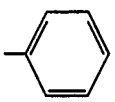 | Cl | H | H | Cl | H | 112 |
| 83 | $-CH_3$ | H | H | H | Cl | H | 112 |
| 84 | $-CH_2Cl$ | H | H | H | Cl | H | 77 |
| 85 | 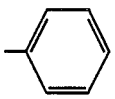 | H | H | H | Cl | H | 113 |
| 86 | 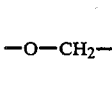 | H | H | H | Cl | H | 101 |
| 87 | 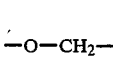 | Cl | H | H | Cl | H | 77 |
| 88 | 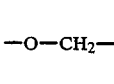 | Cl | H | F | Cl | H | 126 |

Preparation of the starting substances

Example 1A

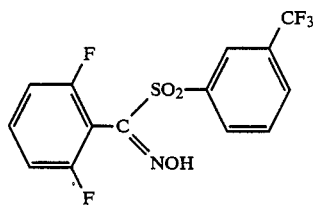

19.2 g (0.1 m) of α-chloro-2,6-difluoro-benzaldoxime are dissolved in 200 ml of methanol, and 23.2 g (0.1 m) of sodium 3-trifluoromethylbenzensulphinate are added at room temperature. The reaction mixture is kept at this temperature for about 15 hours and is then poured onto 1 l of ice-water and extracted by stirring, and the product is filtered off with suction, washed and dried. The reaction product is recrystallized from toluene. 24 g (62.5% of theory) of α-3-trifluoromethylphenylsulphonyl-2,6-difluorobenzaldoxime of melting point 127° C. are obtained.

The following compounds of the formula (II)

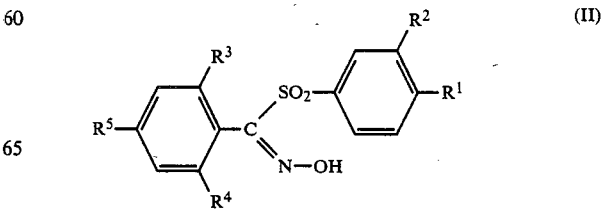

(II)

can be prepared analogously:

| Example | R¹ | R² | R³ | R⁴ | R⁵ | Physical data (melting point °C.) |
|---|---|---|---|---|---|---|
| 2 A | CH₃ | H | H | Cl | Cl | 143 |
| 3 A | Cl | H | Cl | F | H | 158 |
| 4 A | CH₃ | H | Cl | F | H | 170 |
| 5 A | H | H | Cl | F | H | 143 |
| 6 A | OCH₃ | H | Cl | F | H | 145 |
| 7 A | CH₃ | H | H | Cl | H | 147 |
| 8 A | H | H | Cl | Cl | H | 148 |
| 9 A | F | H | Cl | Cl | H | 154 |
| 10 A | Cl | H | Cl | Cl | H | 111 |
| 11 A | H | H | F | F | H | 149 |
| 12 A | Cl | H | F | F | H | 171 |
| 13 A | CH₃ | H | F | F | H | 166 |
| 14 A | OCH₃ | H | Cl | Cl | H | 163 |
| 15 A | —OCH₃ | H | F | F | H | 145 |
| 16 A | —OCH₃ | H | Cl | H | H | 141 |
| 17 A | H | CF₃ | Cl | Cl | H | 148 |

It will be understood that the specification and examples are illustrative but not limitative of the present invention and that other embodiments within the spirit and scope of the invention will suggest themselves to those skilled in the art.

We claim:

1. A benzaldoxime derivative of the formula

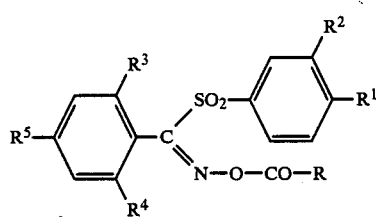

in which
R represents straight-chain or branched alkyl with 1 to 6 carbon atoms, or represents straight-chain or branched alkoxy with 1 to 6 carbon atoms, or represents halogenoalkyl or halogenoalkoxy with in each case 1 to 6 carbon atoms in the straight-chain or branched halogenoalkyl radical and 1 to 9 identical or different halogen atoms, or represents straight-chain or branched alkenyloxy with 2 to 6 carbon atoms, or represents aryl or aryloxy which have 6 to 10 carbon atoms and are unsubstituted or in each case substituted by one to five identical or different substituents from the group comprising straight-chain or branched alkyl with 1 to 4 carbon atoms, straight-chain or branched alkoxy with 1 to 4 carbon atoms, halogen, nitro and acetyl, or represents aralkyloxy which has 6 to 12 carbon atoms in the aryl radical and 1 to 6 carbon atoms in the straight-chain or branched alkyl radical and is unsubstituted or substituted by one to five identical or different substituents from the group comprising straight-chain or branched alkyl and alkoxy with 1 to 4 carbon atoms, halogen, nitro and acetyl, or represents cycloalkoxy which has 5 to 7 carbon atoms in the cycloalkyl part and is unsubstituted or substituted by one to five identical or different substituents from the group comprising straight-chain or branched alkyl with 1 to 4 carbon atoms, or represents a saturated or partly or completely unsaturated heterocyclic radical which has 5 to 8 ring members, can contain 1 to 3 hetero atoms and is unsubstituted or substituted by one to three identical or different substituents from the group comprising straight-chain or branched alkyl with 1 to 4 carbon atoms;

R¹ represents hydrogen, halogen, straight-chain or branched alkyl with 1 to 6 carbon atoms or straight-chain or branched alkoxy with 1 to 6 carbon atoms, and R² represents hydrogen or straight-chain or branched alkyl with 1 to 6 carbon atoms, or represents straight-chain or branched halogenoalkyl with 1 to 6 carbon atoms and 1 to 9 identical or different halogen atoms.

2. A benzaldoxime derivative according to claim 1, in which
R represents straight-chain or branched alkyl with 1 to 4 carbon atoms, or represents straight-chain or branched alkoxy with 1 to 4 carbon atoms, or represents halogenoalkyl or halogenoalkoxy with in each case 1 to 4 carbon atoms in the straight-chain or branched halogenoalkyl radical and 1 to 5 identical or different halogen atoms, or represents straight-chain or branched alkenyloxy with 2 to 5 carbon atoms, or represents phenyl or phenoxy which are unsubstituted or in each case substituted by one to five identical or different substituents from the group comprising straight-chain or branched alkyl with 1 to 3 carbon atoms, straight-chain or branched alkoxy with 1 to 3 carbon atoms, halogen, nitro and acetyl, or represents benzyloxy, phenethyloxy or phenylpropyloxy which are unsubstituted or substituted by one to three identical or different substituents from the group comprising straight-chain or branched alkyl and alkoxy with 1 to 3 carbon atoms, halogen, nitro and acetyl, or represents cycloalkoxy which has 5 to 7 carbon atoms in the cycloalkyl part and is unsubstituted or substituted by one to three identical or different substituents from the group comprising straight-chain or branched alkyl with 1 to 3 carbon atoms, or represents a saturated, partly saturated or unsaturated heterocyclic radical which has 5 to 7 ring members, can contain 1 or 2 sulphur, nitrogen and/or oxygen atoms and is unsubstituted or monosubstituted by straight-chain or branched alkyl with 1 to 3 carbon atoms;

R¹ represents hydrogen, halogen, straight-chain or branched alkyl with 1 to 4 carbon atoms or straight-chain or branched alkoxy with 1 to 4 carbon atoms, and R² represents hydrogen or straight-chain or branched alkyl with 1 to 4 carbon atoms, or represents straight-chain or branched halogenoalkyl with 1 to 4 carbon atoms and 1 to 5 identical or different halogen atoms.

3. A benzaldoxime derivative according to claim 1, in which
R represents straight-chain or branched alkyl with 1 to 6 carbon atoms, or represents straight-chain or branched alkoxy with 1 to 6 carbon atoms, or represents halogenoalkyl or halogenoalkoxy with in each case 1 or 2 carbon atoms in the halogenoalkyl radical and 1 to 4 identical or different halogen atoms, or represents straight-chain or branched alkenyloxy with 2 or 3 carbon atoms, or represents phenyl or phenoxy which are unsubstituted or in each case substituted by one or two identical or different substituents from the group comprising alkyl with 1 or 2 carbon atoms, alkoxy with 1 or 2 carbon atoms, halogen, nitro and acetyl, or represents benzyl which is unsubstituted or substituted by one to three identical or different substituents from the group containing alkyl and alkoxy with 1 or 2 carbon atoms and halogen, or represents cycloalkoxy which has 5 or 6 carbon atoms in the cycloalkyl part and is unsubstituted or substituted by one to three identical or different substituents from the group comprising alkyl with 1 or 2 carbon atoms, or represents an unsaturated heterocyclic radical which has 5 or 6 ring members, can contain nitrogen atom and/or a sulphur atom and is unsubstituted or substituted by one or two identical or different substituents from the group comprising alkyl with 1 or 2 carbon atoms;

$R^1$ represents hydrogen, halogen, alkyl with 1 or 2 carbon atoms or alkoxy with 1 or 2 carbon atoms, and $R^2$ represents hydrogen or alkyl with 1 or 2 carbon atoms, or represents halogenoalkyl with 1 or 2 carbon atoms and 1 to 3 identical or different halogen atoms.

4. A benzaldoxime derivative according to claim 1, in which

R represents methyl, ethyl, methoxy, ethoxy, n-propoxy, iso-propoxy, iso-butoxy, allyloxy, 2,2,2-trichloroethoxy, benzyloxy, chloromethyl, phenyl, 2,6-dichlorophenyl, 2,4-dichlorophenyl, phenoxy, thienyl or cyclohexyloxy, $R^1$ represents hydrogen, fluorine, chlorine, methyl or methoxy, $R^2$ represents hydrogen or trifluoromethyl, $R^3$ represents hydrogen, fluorine or chlorine, $R^4$ represents fluorine or chlorine and $R^5$ represents hydrogen or chlorine.

5. A compound according to claim 1 wherein such compound is

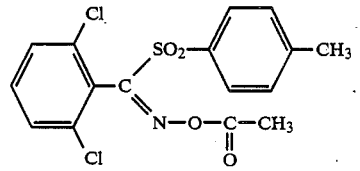

6. A compound according to claim 1 wherein such compound is

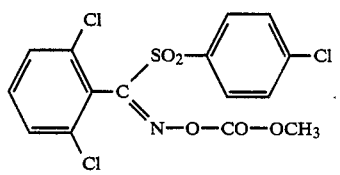

7. A compound according to claim 1 wherein such compound is

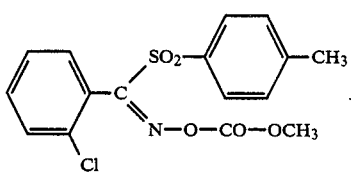

8. A compound according to claim 1 wherein such compound is

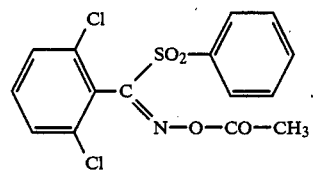

9. A compound according to claim 1 wherein such compound is

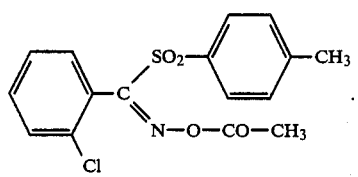

10. A fungicidal composition comprising a fungicidally effective amount of a compound according to claim 1 and a diluent.

11. A method of combating fungi which comprises applying to such fungi or to a fungus habitat a fungicidally effective amount of a compound according to claim 1.

12. The method according to claim 11, wherein such compound is

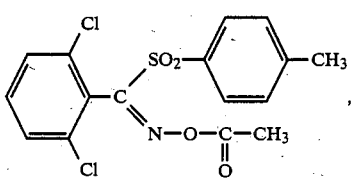

,

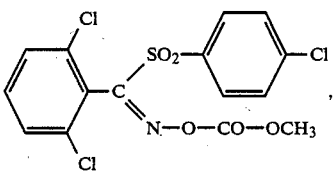

,

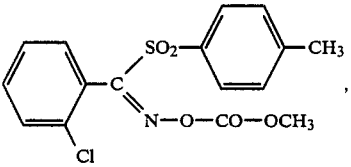

,

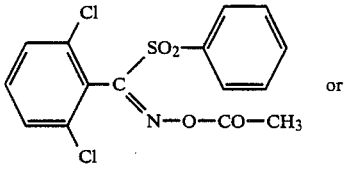

or

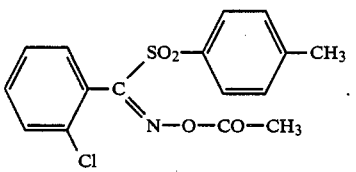

* * * * *

UNITED STATES PATENT AND TRADEMARK OFFICE
CERTIFICATE OF CORRECTION

PATENT NO. : 4,886,832

DATED : December 12, 1989

INVENTOR(S) : Fest et al.

It is certified that error appears in the above-identified patent and that said Letters Patent is hereby corrected as shown below:

Title Page — U.S. PATENT DOCUMENTS: Delete " 4,747,678 " and substitute -- 4,746,678 --

Col. 18, claim 1 line 8 — After " atoms, " delete " and "

Col. 18, claim 1 line 13 — After line 13 " atoms " add --
$R^3$ represents hydrogen or halogen,
$R^4$ represents halogen and
$R^5$ represents hydrogen or halogen Col. 19, claim 3 line 6 — Delete " containing " and substitute -- comprising --

Signed and Sealed this

Thirty-first Day of March, 1992

Attest:

HARRY F. MANBECK, JR.

Attesting Officer

Commissioner of Patents and Trademarks